(12) United States Patent
Jordan

(10) Patent No.: US 8,715,630 B2
(45) Date of Patent: May 6, 2014

(54) SILICONE REPLACEMENTS FOR PERSONAL CARE COMPOSITIONS

(75) Inventor: Susan L. Jordan, Doylestown, PA (US)

(73) Assignee: Dow Global Technologies LLC, Midland, MI (US)

(*) Notice: Subject to any disclaimer, the term of this patent is extended or adjusted under 35 U.S.C. 154(b) by 0 days.

(21) Appl. No.: 12/882,320

(22) Filed: Sep. 15, 2010

(65) Prior Publication Data

US 2011/0064685 A1 Mar. 17, 2011

Related U.S. Application Data

(60) Provisional application No. 61/242,495, filed on Sep. 15, 2009.

(51) Int. Cl.
*A61K 8/81* (2006.01)
*A61Q 5/02* (2006.01)
*A61Q 5/12* (2006.01)

(52) U.S. Cl.
USPC ............... 424/70.11; 424/63; 424/70.16

(58) Field of Classification Search
USPC ........... 424/70.11, 63, 70.16, 70.9; 514/188, 514/163; 3/70.11, 63, 70.16, 70.9
See application file for complete search history.

(56) References Cited

U.S. PATENT DOCUMENTS

| | | | |
|---|---|---|---|
| 2,174,761 A | 10/1939 | Schuette et al. | |
| 2,677,700 A | 5/1954 | Jackson et al. | |
| 2,915,559 A | 12/1959 | Horsley et al. | |
| 4,019,990 A | 4/1977 | Marshall et al. | |
| 4,134,841 A | 1/1979 | Park et al. | |
| 4,272,395 A | 6/1981 | Wright | |
| 4,280,919 A | 7/1981 | Stoeckigt et al. | |
| 4,340,382 A | 7/1982 | Morlino et al. | |
| 4,343,616 A | 8/1982 | Decker et al. | |
| 4,410,447 A | 10/1983 | Decker et al. | |
| 4,599,392 A | 7/1986 | McKinney et al. | |
| 4,701,432 A | 10/1987 | Welborn, Jr. | |
| 4,784,798 A | 11/1988 | Geke et al. | |
| 4,965,014 A | 10/1990 | Jeschke et al. | |
| 4,968,450 A | 11/1990 | Kamegai et al. | |
| 4,988,781 A | 1/1991 | McKinney et al. | |
| 5,272,236 A | 12/1993 | Lai et al. | |
| 5,322,728 A | 6/1994 | Davey et al. | |
| 5,384,373 A | 1/1995 | McKinney et al. | |
| 5,705,476 A | 1/1998 | Hoffarth | |
| 5,707,948 A | 1/1998 | Evers et al. | |
| 5,726,137 A * | 3/1998 | Patel et al. | 510/122 |
| 5,767,056 A | 6/1998 | Lenoir | |
| 5,981,455 A | 11/1999 | Carrie et al. | |
| 6,048,831 A | 4/2000 | Mori et al. | |
| 6,429,342 B1 | 8/2002 | Clement et al. | |
| 6,525,157 B2 | 2/2003 | Cozewith et al. | |
| 6,602,823 B1 | 8/2003 | Rochling et al. | |
| 6,960,635 B2 | 11/2005 | Stevens et al. | |
| 7,012,052 B1 | 3/2006 | Kluesener et al. | |
| 7,160,397 B2 | 1/2007 | Bergstrom | |
| 7,332,465 B2 | 2/2008 | Wulff et al. | |
| 7,560,494 B2 | 7/2009 | Steinbrenner et al. | |
| 2003/0202952 A1 * | 10/2003 | Wells et al. | 424/70.13 |
| 2005/0027626 A1 | 2/2005 | Garcia | |
| 2005/0170991 A1 | 8/2005 | Ruland et al. | |
| 2007/0292705 A1 * | 12/2007 | Moncla et al. | 428/523 |
| 2007/0295465 A1 | 12/2007 | Dyer et al. | |

FOREIGN PATENT DOCUMENTS

| | | |
|---|---|---|
| GB | 1097491 | 1/1968 |
| GB | 2145726 | 4/1985 |
| WO | 9618712 | 6/1996 |
| WO | 03/082232 A1 | 10/2003 |
| WO | 2009/064739 A1 | 5/2009 |

OTHER PUBLICATIONS

MSDS (Polyquaternium-7; New Directions Laboratory Oct. 2008).*

* cited by examiner

*Primary Examiner* — Anoop Singh
*Assistant Examiner* — Anna Falkowitz
(74) *Attorney, Agent, or Firm* — Edward L. Brant

(57) ABSTRACT

Described are personal care compositions, comprising an aqueous dispersion comprising a metallocene catalyzed polyolefin and an ethylene acrylic acid copolymer; a cationic polymer; and a least one cosmetically acceptable surfactant, emollient, or cosmetic active, provided that the personal care composition contains less than 0.09 wt % of silicone, and preferably is substantially free of silicone.

7 Claims, No Drawings

SILICONE REPLACEMENTS FOR PERSONAL CARE COMPOSITIONS

CROSS-REFERENCE TO RELATED APPLICATION(S)

This application claims benefit of priority from U.S. Provisional Patent Application No. 61/242,495, filed Sep. 15, 2009, which application is incorporated by reference herein to its entirety.

FIELD

The present application relates to personal care compositions.

BACKGROUND

Silicone deposition is known to increase perceptions of smoothness in personal care compositions, particularly conditioners, shampoos, and body washes.

However, it is a major challenge in the art to balance the personal care components in a way that promotes silicone deposition, as opposed to encouraging the silicone to wash off. One alternative is to develop new formulations that offer similar aesthetic properties to silicones, but without silicones. Thus, it is an important goal in the art to create such new formulations.

SUMMARY

In one embodiment, the present invention provides personal care compositions, comprising an aqueous dispersion comprising a metallocene catalyzed polyolefin and an ethylene acrylic acid copolymer; a cationic polymer; and at least one cosmetically acceptable surfactant, emollient, or cosmetic active, provided that the personal care composition contains less than 0.09 wt % of silicone, and preferably is substantially free of silicone.

DETAILED DESCRIPTION

In one embodiment, the present invention provides personal care compositions, comprising an aqueous dispersion comprising a metallocene catalyzed polyolefin and an ethylene acrylic acid copolymer; a cationic polymer; and at least one cosmetically acceptable surfactant, emollient, or cosmetic active, provided that the personal care composition contains less than 0.09 wt % of silicone, and preferably is substantially free of silicone.

"Personal care" relates to compositions to be topically applied to a person (including mouth, ear, and nasal cavities, but not ingested). Examples of personal care compositions include skin care products (e.g., facial cream, moisturizers, leave on and rinse off lotions, sunscreens, foundation, mascara, eye-liner, lipstick, cleansers, and the like) and hair care products (including shampoos, leave on and rinse off conditioners, styling gels and hairsprays). Preferably, the personal care composition is a shampoo, a rinse-off conditioner, a leave-in conditioner, or a body wash.

"Cosmetically acceptable" refers to ingredients typically used in personal care compositions, and is intended to underscore that materials that are toxic when present in the amounts typically found in personal care compositions are not contemplated as part of the present invention.

Copolymerizing ethylene with acrylic acid yields ethylene-acrylic acid (EAA) copolymers, which are known as flexible thermoplastics for blister packaging and the like. A preferred ethylene acrylic acid copolymer comprises greater than about 15 wt % acrylic acid, preferably greater than about 17 wt % acrylic acid, more preferably about 20 wt % acrylic acid. It should be understood that ranges recited in this disclosure include all subcombinations of ranges.

A preferred EAA copolymer is PRIMACOR 5990 copolymer (20 wt % acrylic acid), which has a melt index of 1300 g/10 minute (ASTM Method D-1238 at 190° C.) and a Brookfield viscosity of 13,000 cps at 350° F., and is available from The Dow Chemical Company. Another preferred EAA copolymer is PRIMACOR 5980i copolymer (20.5 wt % acrylic acid), which has a melt index of 300 g/10 minute (ASTM Method D-1238 at 190° C.), available from The Dow Chemical Company. EAA copolymers are also available under the tradename NUCREL 2806, available from E.I. du Pont de Nemours and Company, Inc. Ethylene-acrylic acid and ethylene-methacrylic acid copolymers, are described in U.S. Pat. Nos. 4,599,392, 4,988,781, and 5,938,437, each of which is incorporated herein by reference in its entirety.

Metallocene catalyzed polyolefins are polyolefins produced with a metallocene catalyst as described in U.S. Pat. Nos. 4,701,432, 5,322,728, and 5,272,236, each of which is incorporated herein by reference in its entirety. As a specific embodiment of the present invention, the metallocene catalyzed polyolefins are polyethylenes produced with a metallocene catalyst. Such metallocene catalyzed polyethylenes are available e.g. from The Dow Chemical Company under the trademark AFFINITY or ENGAGE (ethylene/octene copolymers) and from Exxon Chemical Company under the trademark EXACT (ethylene/butene copolymers, ethylene/hexene copolymers, or ethylene/butene/hexene terpolymers). In one embodiment, the metallocene catalyzed polyolefin is at least one of ethylene/octene copolymers, ethylene/butene copolymers, ethylene/hexene copolymers, ethylene/propylene or ethylene/butene/hexene terpolymers, preferably an ethylene octene copolymer. In another embodiment, the metallocene catalyzed polyolefin is a propylene/alpha-olefin copolymer, which is further described in details in the U.S. Pat. Nos. 6,960,635 and 6,525,157, each of which is incorporated herein by reference in its entirety. Such propylene/alpha-olefin copolymers are commercially available from The Dow Chemical Company, under the tradename VERSIFY™, or from ExxonMobil Chemical Company, under the tradename VISTAMAXX™.

In one embodiment, the ethylene acrylic acid copolymer and metallocene catalyzed polyolefin are melt-kneaded in an extruder along with water and a neutralizing agent, such as ammonia, potassium hydroxide, or a combination of the two, to form an aqueous dispersion.

Mechanical dispersion, such as a Parr reactor, is used to create the aqueous dispersion.

The ethylene acrylic acid copolymer is present in a range from about 2 wt % to about 35 wt % by weight of the aqueous dispersion, preferably in a range from about 4 wt % to about 20 wt %.

In one embodiment, the metallocene catalyzed polyolefin is present in a range from about 10 wt % to about 50 wt % by weight of the aqueous dispersion, preferably in a range from about 15 wt % to about 40 wt %.

Typically, the ethylene acrylic acid copolymer and metallocene catalyzed polyolefin is in a polymer ratio of about 40:60 to about 15:85.

The solids content of the aqueous dispersion is in a range from about 10% by weight to about 50% by weight, preferably about 40% by weight.

In turn, the aqueous dispersion is present in a range from about 0.5 wt % to about 10 wt % of solids, preferably about 1 wt % to about 5 wt %, by weight of the personal care composition.

In one embodiment, the cationic polymer is a polysaccharide modified to have a positive charge, for example, cationic cellulose derivatives (including, for example PQ10, PQ24, and PQ 67), cationic guar derivatives, cationic methacrylamido polymers, and synthetic cationic polymers such as PQ6 and PQ7. In a preferred embodiment, the cationic polymer is cationically modified hydroxyethylcellulose, which is commercially available from The Dow Chemical Company under the tradename UCARE. The cationic polymer is present in a range from about 0.05 wt % to about 5 wt %, preferably about 0.1 wt % to about 2 wt %, by weight of the personal care composition.

In one embodiment, the surfactant is an anionic, nonionic, or amphoteric surfactant, or a mixture thereof.

In one embodiment, the surfactant is a detergent surfactant. In this embodiment, the surfactant is present in an amount from about 2% to about 30% by weight of the composition, preferably from about 5% to about 25% by weight of the composition, most preferably from about 7% to about 20% by weight of the composition.

Preferably, the detergent surfactant is an anionic surfactant in combination with an amphoteric surfactant. In one embodiment, the anionic surfactant is ammonium laureth sulfate, ammonium lauryl sulfate, sodium laureth sulfate, or sodium lauryl sulfate. In one embodiment, the anionic surfactant is present in an amount from about 1% to about 25%, preferably from about 5% to about 20%, more preferably from about 7% to about 15%, by weight of the composition.

In one embodiment, the mixture is an anionic surfactant in combination with a second surfactant that is disodium cocoamphodiacetate, decylglucoside, or cocamidopropyl betaine. In one embodiment, the second surfactant is present in an amount from about 1% to about 10%, preferably from about 1% to about 8%, more preferably from about 2% to about 6%, by weight of the composition.

In a preferred embodiment, the surfactant is a mixture of sodium laureth sulfate (such as is commercially available from Cognis as under the tradename STANDAPOL ES) and disodium cocoamphodiacetate (such as is commercially available from Henkel as under the tradename VELVETEX CDC). When the surfactant is a mixture of sodium laureth sulfate and disodium cocoamphodiacetate, the ratio of sodium laureth sulfate to disodium cocoamphodiacetate is in a range from about 9:1 to about 2:1, most preferably about 6:1.

In one embodiment, the composition includes citric acid to adjust the pH.

Other optional ingredients for personal care compositions of the present invention include cosmetically acceptable emollients, sunscreens, surfactants, emulsifiers, preservatives, rheology modifiers, colorants, dyes, preservatives, pH adjustors, propellants, reducing agents, fragrances, foaming agents, tanning agents, depilatory agents, flavors, astringents, antiseptics, deodorants, antiperspirants, insect repellants, bleaches, lighteners, anti-dandruff agents, adhesives, polishes, strengtheners, fillers, barrier materials, or biocides.

In some embodiments, the personal care composition further comprises an optional rheology modifier as a thickener. Examples of thickeners include polymers, for example, modified or unmodified carboxyvinyl polymers, such as the products sold under the names CARBOPOL and PEMULEN (INCI name: Acrylates/$C_{10\text{-}30}$ alkyl acrylate crosspolymer; available from Noveon), polyacrylates and polymethacrylates, such as the products sold under the names LUBRAJEL and NORGEL (commercially available from Guardian) or HISPAGEL (commercially available from Hispano Chimica), polyacrylamides, 2-acrylamido-2-methylpropane-sulfonic acid polymers and polymers, which are optionally crosslinked and/or neutralized, for instance the poly(2-acrylamido-2-methylpropane-sulfonic acid) sold by Clariant (INCI name: ammonium polyacryldimethyltauramide), emulsified crosslinked anionic polymers of acrylamide and AMPS, such as those sold under the name SEPIGEL 305 (INCI name: Polyacrylamide/C13-14 Isoparaffin/Laureth-7; from Seppic) and under the name SIMULGEL 600 (INCI name: Acrylamide/Sodium acryloyldimethyltaurate polymer/Isohexadecane/Polysorbate 80; from Seppic), polysaccharide biopolymers, for instance xanthan gum, guar gum, carob gum, acacia gum, scleroglucans, chitin and chitosan derivatives, carrageenans, gellans, alginates, celluloses such as microcrystalline cellulose, cellulose derivatives, associative polymers, for instance associative polyurethanes, polymers comprising at least two hydrocarbon-based lipophilic chains comprising from 6 to 30 carbon atoms, separated with a hydrophilic sequence, such as the polyurethanes sold under the names SERAD FX1010, SERAD FX1100 and SERAD FX1035 (commercially available from Hüls America), RHEOLATE 255, RHEOLATE 278 and RHEOLATE 244 (INCI name: Polyether-urea-polyurethane; from Rheox), DW 1206F, DW 1206J, DW 1206B, DW 1206G, and ACRYSOL RM 2020 (commercially available from Röhm & Haas).

Colorants include pigments, which are used especially in make-up, including metal oxide pigments, titanium dioxide, optionally surface-treated, zirconium oxide or cerium oxide, zinc oxide, iron oxide (black, yellow or red), chromium oxide, manganese violet, ultramarine blue, chromium hydrate and ferric blue, carbon black, pigments of barium, strontium, calcium or aluminum (for example D&C or FD&C), cochineal carmine, mica coated with titanium or with bismuth oxychloride, titanium mica with iron oxides, titanium mica with, especially, ferric blue or chromium oxide, titanium mica with an organic pigment, nacreous pigments based on bismuth oxychloride, goniochromatic pigments, for example pigments with a multilayer interference structure, reflective pigments, for example particles with a silver-coated glass substrate, glass substrate coated with nickel/chromium/molybdenum alloy, glass substrate coated with brown iron oxide, particles comprising a stack of at least two polymer layers, for instance MIRROR GLITTER (commercially available from 3M).

Dyes include water-soluble dyes such as copper sulfate, iron sulfate, water-soluble sulfopolyesters, rhodamines, natural dyes, for instance carotene and beetroot juice, methylene blue, caramel, the disodium salt of tartrazine and the disodium salt of fuschin, and mixtures thereof. Liposoluble dyes from the list above may also optionally be used.

Preservatives include alcohols, aldehydes, methylchloroisothiazolinone and methylisothiazolinone, p-hydroxybenzoates, and in particular methylparaben, propylparaben, glutaraldehyde and ethyl alcohol.

The pH adjustors, include inorganic and organic acids and bases and in particular aqueous ammonia, citric acid, phosphoric acid, acetic acid, and sodium hydroxide.

Reducing agents include ammonium thioglycolate, hydroquinone and sodium thioglycolate.

Fragrances may be aldehydes, ketones, or oils obtained by extraction of natural substances or synthetically produced as described above. Often, fragrances are accompanied by auxiliary materials, such as fixatives, extenders, stabilizers and solvents.

Biocides include antimicrobials, bactericides, fungicides, algaecides, mildicides, disinfectants, antiseptics, and insecticides.

The amount of optional ingredients effective for achieving the desired property provided by such ingredients can be readily determined by one skilled in the art.

In use, the personal care compositions are applied to hair or skin. In a preferred embodiment, the personal care composition is a shampoo, body wash, or facial cleanser, preferably a shampoo.

In one embodiment, the present invention provides a method of replacing silicone in a personal care composition, comprising substituting an aqueous dispersion comprising a metallocene catalyzed polyolefin and an ethylene acrylic acid copolymer for the silicone. In one embodiment, the replacement range of personal care composition of claim 1 for silicone is in a range from 0.5:1 to about 2:1.

Silicone includes silicone oils, for instance volatile or non-volatile polymethylsiloxanes (PDMS) comprising a linear or cyclic silicone chain, which are liquid or pasty at room temperature, especially cyclopolydimethylsiloxanes (cyclomethicones) such as cyclopentasiloxane and cyclohexadimethylsiloxane, polydimethylsiloxanes comprising alkyl, alkoxy or phenyl groups, which are pendent or at the end of a silicone chain, these groups comprising from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes 2-phenylethyltrimethyl siloxysilicates and polymethylphenylsiloxanes, fluoro oils such as partially hydrocarbon-based and/or partially silicone-based fluoro oils, preferably dimethicone.

EXAMPLES

The following examples are for illustrative purposes only and are not intended to limit the scope of the present invention. All percentages are by weight unless otherwise specified.

Example 1

Personal care compositions of the present invention include aqueous dispersions comprising an ethylene acrylic acid copolymer. Examples of such aqueous dispersions include the following:

Batch 1

A 41.7% solids aqueous dispersion of ethylene acrylic acid and metallocene catalyzed polyolefin, commercially available from The Dow Chemical Company under the tradename HYPOD 8510, produced using Dow's BLUEWAVE technology.

Example 2

Exemplary personal care shampoo compositions contain the components recited in TABLE 1 on a weight/weight basis (wt. %).

TABLE 1

|  | Batch A | Batch B | Batch C |
|---|---|---|---|
| STANDAPOL ES-2 sodium laureth sulfate | 60.78 | 60.78 | 60.78 |
| VELVETEX CDC disodium cocoamphodiacetate | 6.92 | 6.92 | 6.92 |
| LEXEMUL EGDS pearlizing agent | 2.0 | 2.0 | 2.0 |
| UCARE JR-30M hydroxyethylcellulose (2%) | 12.5 | 12.5 | — |
| JAGUAR C-13S cationic guar (2%) | — | — | 12.5 |
| Batch 1 (41.7%) | 2.4 | 2.4 | 2.4 |
| Citric Acid (10%) | 2.1 | 2.1 | 2.1 |
| GLYDANT DMDM Hydantoin | 0.4 | 0.4 | 0.4 |
| Deionized water | q.s. | q.s. | q.s. |

Combine Batch 1 with base surfactants. Slowly heat to 74° C. while mixing with an overhead stirrer (approximately 500 rpm). Continue stirring until surfactants are in solution. Add pearlizing agent at approximately 500 rpm, maintaining speed for 15 minutes, then cool slowly to about 35° C. Increase stirrer speed to 750 rpm. Stir about 15 minutes. Slowly add cationic polymer and stir about 30 minutes. Add 10% citric acid and stir about 10 min. Add Glydant preservative and q.s. with water to 100 g. Stir 15 min at approximately 500 rpm.

Example 3 (Comparative)

Conventional personal care shampoo compositions contain the components recited in TABLE 2 on a weight/weight basis (wt. %).

TABLE 2

|  | Comp. Batch W | Comp. Batch X | Comp. Batch Y | Comp. Batch Z |
|---|---|---|---|---|
| STANDAPOL ES-2 sodium laureth sulfate | 60.78 | 60.78 | 60.78 | 60.78 |
| VELVETEX CDC disodium cocoamphodiacetate | 6.92 | 6.92 | 6.92 | 6.92 |
| LEXEMUL EGDS pearlizing agent | 2.0 | 2.0 | 2.0 | 2.0 |
| DC 2-1491 Dimethicone Emulsion (60%) | 1.67 | — | — | — |
| DC 1664 trimethyl-trimethylsilyloxy-silane | — | 2.0 | 2.0 | 2.0 |
| UCARE JR-30M hydroxyethylcellulose (2%) | 12.5 | — | 12.5 | — |
| UCARE JR-400 hydroxyethylcellulose (1%) | — | 25 | — | — |
| JAGUAR C-13S cationic guar (2%) | — | — | — | 12.5 |
| Citric Acid (10%) | 2.1 | 2.1 | 2.1 | 2.1 |
| GLYDANT DMDM Hydantoin | 0.4 | 0.4 | 0.4 | 0.4 |
| Deionized water | q.s. | q.s. | q.s. | q.s. |

Slowly heat base surfactants to 74° C. while mixing with an overhead stirrer (approximately 500 rpm). Continue stirring until surfactants are in solution. Add pearlizing agent at approximately 500 rpm, maintaining speed for 15 minutes, then cool slowly to about 35° C. Increase stirrer speed to approximately 750 rpm, slowly add silicone emulsion and stir about 15 minutes. Slowly add cationic polymer and stir about 30 minutes. Add 10% citric acid and stir about 10 min. Add Glydant preservative and q.s. with water to 100 g. Stir 15 min at approximately 500 rpm.

Example 4

Compositions substantially according to the protocols of Examples 2 and 3 were prepared. Pre-washed and pre-hydrated tresses of European 8-hour bleached hair (available from International Hair Importers and Products Inc.) were treated with 0.5 g of these shampoo formulations. The shampoo was worked into the hair for 1 min. and then rinsed off under running tap water at 38° C. at 0.4 gal/min. water flow.

The hair tresses were hung for wet sensory evaluation study. After the tresses were completely dried, dry sensory evaluations were conducted. Ten expert panelists trained to evaluate the performance of cosmetic products on hair were asked to evaluate comb-ability and feel in both the wet and dry stage. Each panelist evaluated a pair of tresses, one tress treated with a composition of the invention versus one treated with a comparative composition. The panelists were asked to pick one tress with superior wet and dry attributes. Results are given in TABLE 3.

TABLE 3

|  | Batch A vs. Comp. Batch W | Batch B vs. Comp. Batch Y |
| --- | --- | --- |
| Wet comb | 60 | 50 |
| Wet feel | 60 | 50 |
| Dry comb | 80 | 40 |
| Dry feel | 80 | 40 |

The results show that the inventive formulations provide statistically the same or better conditioning as silicone polymers.

It is understood that the present invention is not limited to the embodiments specifically disclosed and exemplified herein. Various modifications of the invention will be apparent to those skilled in the art. Such changes and modifications may be made without departing from the scope of the appended claims.

Moreover, each recited range includes all combinations and subcombinations of ranges, as well as specific numerals contained therein. Additionally, the disclosures of each patent, patent application, and publication cited or described in this specification are hereby incorporated by reference herein, in their entireties.

The invention claimed is:

1. A personal care composition, comprising:
   an aqueous mechanical dispersion comprising a metallocene catalyzed polyolefin and an ethylene acrylic acid copolymer combined together in the absence of cationic polymer, wherein the polymer ratio of ethylene acrylic acid copolymer to metallocene catalyzed polyolefin is in a range from 40:60 to 15:85;
   a cationic polymer, wherein the cationic polymer is at least one of cationic cellulose derivatives, cationic guar derivatives, cationic methacrylamido polymers, polyquaternium 6, and polyquaternium 7; and
   at least one cosmetically acceptable surfactant, emollient, or cosmetic active,
   provided that the personal care composition contains less than 0.09 wt % of silicone.

2. The personal care composition of claim 1, wherein the metallocene catalyzed polyolefin comprises at least one of ethylene/octene copolymers, ethylene/butene copolymers, ethylene/hexene copolymers, or ethylene/butene/hexene terpolymers.

3. The personal care composition of claim 1, wherein the ethylene acrylic acid copolymer is present in a range from about 2 wt % to about 35 wt % by weight of the aqueous dispersion.

4. The personal care composition of claim 1, wherein the metallocene catalyzed polyolefin is present in a range from about 10 wt % to about 50 wt % by weight of the aqueous dispersion.

5. The personal care composition of claim 1, wherein the aqueous dispersion is present in a range from about 0.5 wt % to about 10 wt % by weight of the personal care composition.

6. The personal care composition of claim 1, wherein the surfactant is present.

7. The personal care composition of claim 6, wherein the surfactant is present in a range from about 1 wt % to about 30 wt %.

\* \* \* \* \*